United States Patent
Syed et al.

(10) Patent No.: US 11,877,940 B2
(45) Date of Patent: Jan. 23, 2024

(54) MODIFIED FIXED FLAT WIRE BIFURCATED CATHETER AND ITS APPLICATION IN LOWER EXTREMITY INTERVENTIONS

(71) Applicant: RAM MEDICAL INNOVATIONS, LLC, Springfield, OH (US)

(72) Inventors: Mubin I. Syed, Springfield, OH (US); Azim Shaikh, Beavercreek, OH (US); Suresh Pai, Los Altos, CA (US); Celso Bagaoisan, Union City, CA (US)

(73) Assignee: RAM MEDICAL INNOVATIONS, INC., Springfield, OH (US)

( * ) Notice: Subject to any disclaimer, the term of this patent is extended or adjusted under 35 U.S.C. 154(b) by 491 days.

(21) Appl. No.: 17/089,723

(22) Filed: Nov. 5, 2020

(65) Prior Publication Data

US 2021/0045903 A1     Feb. 18, 2021

Related U.S. Application Data (63) Continuation of application No. 16/183,066, filed on Nov. 7, 2018, now Pat. No. 10,857,014.

(Continued)

(51) Int. Cl.
*A61F 2/954*     (2013.01)
*A61M 25/01*     (2006.01)
(Continued)

(52) U.S. Cl.
CPC ........ *A61F 2/954* (2013.01); *A61B 17/32056* (2013.01); *A61F 2/966* (2013.01);
(Continued)

(58) Field of Classification Search
CPC ........ A61B 17/32056; A61B 17/00358; A61B 17/2212; A61F 2/954; A61F 2/966;
(Continued)

(56) References Cited

U.S. PATENT DOCUMENTS

| | | |
|---|---|---|
| 3,896,815 A | 7/1975 | Fettel |
| 4,243,040 A | 1/1981 | Beecher |

(Continued)

FOREIGN PATENT DOCUMENTS

| | | |
|---|---|---|
| CN | 108472124 | 8/2018 |
| CN | 108472472 | 8/2018 |

(Continued)

OTHER PUBLICATIONS

International Search Report and Written Opinion for PCT/US2013/071271 dated Feb. 10, 2014, 7 pages.

(Continued)

*Primary Examiner* — Jocelin C Tanner
(74) *Attorney, Agent, or Firm* — Jennifer Hayes; Nixon Peabody LLP (57) ABSTRACT

A bifurcated catheter and methods of use are disclosed herein. The bifurcated catheter can include a fixed flat wire that is configurable as a stabilization wire. The bifurcated catheter can be configured to improve the initial access and directability by application of a pull force to the stabilization wire, in addition to a push force from the proximal end of the bifurcated catheter. The stabilization wire is anchored once the bifurcated catheter is positioned. The anchored, bifurcated catheter provides stability and pushability to assist the procedural catheter in traversing the tortuous peripheral vasculature.

20 Claims, 9 Drawing Sheets

Related U.S. Application Data (60) Provisional application No. 62/631,904, filed on Feb. 18, 2018.

(51) Int. Cl.
*A61B 17/00* (2006.01)
*A61B 17/3205* (2006.01)
*A61F 2/966* (2013.01)
*A61M 25/06* (2006.01)
*A61B 17/221* (2006.01)

(52) U.S. Cl.
CPC .... *A61M 25/0102* (2013.01); *A61M 25/0108* (2013.01); *A61B 2017/00358* (2013.01); *A61B 2017/2212* (2013.01); *A61M 2025/0177* (2013.01); *A61M 2025/0681* (2013.01)

(58) Field of Classification Search
CPC .............. A61M 25/0082; A61M 25/01; A61M 25/0102; A61M 25/0108; A61M 2025/0096; A61M 2025/0177; A61M 2025/0681
See application file for complete search history.

(56) References Cited

U.S. PATENT DOCUMENTS

| | | | |
|---|---|---|---|
| 4,790,331 A | 12/1988 | Okada et al. | |
| 5,098,707 A | 3/1992 | Baldwin et al. | |
| 5,293,772 A | 3/1994 | Carr, Jr. | |
| 5,344,426 A | 9/1994 | Lau et al. | |
| 5,419,777 A | 5/1995 | Hofling | |
| 5,433,705 A | 7/1995 | Giebel et al. | |
| 5,571,135 A | 11/1996 | Fraser et al. | |
| 5,651,366 A | 7/1997 | Liang et al. | |
| 5,653,743 A | 8/1997 | Martin | |
| 5,662,703 A | 9/1997 | Yurek et al. | |
| 5,669,924 A | 9/1997 | Shaknovich | |
| 5,690,644 A | 11/1997 | Yurek et al. | |
| 5,718,702 A | 2/1998 | Edwards | |
| 5,720,735 A * | 2/1998 | Dorros | A61M 25/0021 604/284 |
| 5,766,192 A | 6/1998 | Zacca | |
| 5,807,330 A | 9/1998 | Teitelbaum | |
| 5,813,976 A | 9/1998 | Filipi et al. | |
| 5,824,055 A | 10/1998 | Spiridigliozzi | |
| 5,957,901 A | 9/1999 | Mottola et al. | |
| 5,997,563 A | 12/1999 | Kretzers | |
| 6,027,462 A | 2/2000 | Greene et al. | |
| 6,059,813 A | 5/2000 | Vrba et al. | |
| 6,070,589 A | 6/2000 | Keith et al. | |
| 6,152,141 A | 11/2000 | Stevens et al. | |
| 6,224,587 B1 * | 5/2001 | Gibson | A61M 25/0147 604/528 |
| 6,238,410 B1 | 5/2001 | Vrba et al. | |
| 6,245,017 B1 | 6/2001 | Hashimoto | |
| 6,245,573 B1 | 6/2001 | Spillert | |
| 6,428,567 B2 | 8/2002 | Wilson et al. | |
| 6,450,964 B1 | 9/2002 | Webler | |
| 6,464,665 B1 | 10/2002 | Heuser | |
| 6,494,875 B1 | 12/2002 | Mauch | |
| 6,544,278 B1 | 4/2003 | Vrba et al. | |
| 6,652,556 B1 | 11/2003 | Vantassel | |
| 6,663,613 B1 | 12/2003 | Lewis et al. | |
| 6,764,505 B1 | 7/2004 | Hossainy et al. | |
| 6,780,174 B2 | 8/2004 | Mauch | |
| 6,808,520 B1 | 10/2004 | Fouirkas et al. | |
| 6,837,881 B1 | 1/2005 | Barbut | |
| 6,929,633 B2 | 8/2005 | Evans et al. | |
| 6,932,829 B2 | 8/2005 | Majercak | |
| 6,942,682 B2 | 9/2005 | Vrba et al. | |
| 7,235,083 B1 * | 6/2007 | Perez | A61F 2/954 623/1.11 |
| 7,393,358 B2 | 7/2008 | Malewicz | |
| 7,651,520 B2 | 1/2010 | Fischell et al. | |
| 7,674,493 B2 | 3/2010 | Hossainy et al. | |
| 7,740,791 B2 | 6/2010 | Kleine et al. | |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,828,832 B2 | 11/2010 | Belluche et al. | |
| 7,842,026 B2 | 11/2010 | Cahill et al. | |
| 7,955,370 B2 | 6/2011 | Gunderson | |
| 8,092,509 B2 | 1/2012 | Dorn et al. | |
| 8,119,184 B2 | 2/2012 | Hossainy et al. | |
| 8,202,309 B2 | 6/2012 | Styrc | |
| 8,241,241 B2 | 8/2012 | Evans et al. | |
| 8,343,181 B2 | 1/2013 | Duffy et al. | |
| 8,419,767 B2 | 4/2013 | Al-Qbandi et al. | |
| 8,535,290 B2 | 9/2013 | Evans et al. | |
| 8,721,714 B2 | 5/2014 | Kelley | |
| 8,727,988 B2 | 5/2014 | Flaherty et al. | |
| 8,728,144 B2 | 5/2014 | Fearnot | |
| 8,740,971 B2 | 6/2014 | Iannelli | |
| 8,986,241 B2 | 3/2015 | Evans et al. | |
| 8,998,894 B2 | 4/2015 | Mauch et al. | |
| 9,301,830 B2 | 4/2016 | Heuser et al. | |
| 9,314,499 B2 | 4/2016 | Wang et al. | |
| 9,414,824 B2 | 8/2016 | Fortson | |
| 9,636,244 B2 | 5/2017 | Syed | |
| 9,855,705 B2 | 1/2018 | Wang et al. | |
| 9,980,838 B2 | 5/2018 | Syed | |
| 10,492,936 B2 | 12/2019 | Syed | |
| 10,779,976 B2 | 9/2020 | Syed | |
| 10,857,014 B2 * | 12/2020 | Syed | A61M 25/0102 |
| 10,888,445 B2 | 1/2021 | Syed | |
| 11,007,075 B2 | 5/2021 | Bagoaisan | |
| 11,020,256 B2 | 6/2021 | Syed | |
| 2001/0003985 A1 | 6/2001 | Lafontaine et al. | |
| 2001/0049534 A1 | 12/2001 | Lachat | |
| 2002/0077691 A1 | 6/2002 | Nachtigall | |
| 2002/0123698 A1 | 9/2002 | Garibotto et al. | |
| 2002/0156518 A1 | 10/2002 | Tehrani | |
| 2002/0165535 A1 | 11/2002 | Lesh | |
| 2003/0088187 A1 | 5/2003 | Saadat et al. | |
| 2003/0204171 A1 | 10/2003 | Kucharczyk | |
| 2003/0216721 A1 | 11/2003 | Diederich | |
| 2003/0229282 A1 | 12/2003 | Burdette | |
| 2004/0002714 A1 | 1/2004 | Weiss | |
| 2004/0073190 A1 | 4/2004 | Deem et al. | |
| 2004/0127975 A1 * | 7/2004 | Levine | A61B 17/12172 623/1.11 |
| 2004/0138734 A1 | 7/2004 | Chobotov et al. | |
| 2004/0147837 A1 | 7/2004 | Macaulay et al. | |
| 2004/0167463 A1 * | 8/2004 | Zawacki | A61M 25/0026 604/43 |
| 2005/0043779 A1 | 2/2005 | Wilson | |
| 2005/0101968 A1 | 5/2005 | Dadourian | |
| 2005/0113798 A1 | 5/2005 | Slater | |
| 2005/0113862 A1 * | 5/2005 | Besselink | A61M 25/04 606/200 |
| 2005/0222488 A1 | 10/2005 | Chang et al. | |
| 2005/0234499 A1 | 10/2005 | Olson et al. | |
| 2005/0251160 A1 | 11/2005 | Saadat et al. | |
| 2005/0267010 A1 | 12/2005 | Goodson et al. | |
| 2006/0025752 A1 | 2/2006 | Broaddus et al. | |
| 2006/0025844 A1 | 2/2006 | Majercak et al. | |
| 2006/0030923 A1 | 2/2006 | Gunderson | |
| 2006/0036218 A1 * | 2/2006 | Goodson | A61M 25/04 604/264 |
| 2006/0074484 A1 | 4/2006 | Huber | |
| 2006/0155363 A1 | 7/2006 | Laduca et al. | |
| 2006/0200221 A1 | 9/2006 | Malewicz | |
| 2006/0257389 A1 | 11/2006 | Binford | |
| 2006/0259063 A1 | 11/2006 | Bates et al. | |
| 2006/0270900 A1 | 11/2006 | Chin et al. | |
| 2007/0016019 A1 | 1/2007 | Salgo | |
| 2007/0016062 A1 | 1/2007 | Park | |
| 2007/0038061 A1 | 2/2007 | Huennekens et al. | |
| 2007/0038293 A1 | 2/2007 | St. Goar et al. | |
| 2007/0049867 A1 | 3/2007 | Shindelman | |
| 2007/0083215 A1 | 4/2007 | Hamer et al. | |
| 2007/0118151 A1 | 5/2007 | Davidson et al. | |

(56) References Cited

U.S. PATENT DOCUMENTS

| | | |
|---|---|---|
| 2007/0129719 A1 | 6/2007 | Kendale et al. |
| 2007/0219614 A1 | 9/2007 | Hartley et al. |
| 2007/0288082 A1 | 12/2007 | Williams |
| 2008/0009829 A1 | 1/2008 | Ta |
| 2008/0039746 A1 | 2/2008 | Hissong et al. |
| 2008/0114239 A1 | 5/2008 | Randall et al. |
| 2008/0172122 A1* | 7/2008 | Mayberry ............... A61F 2/954 623/1.15 |
| 2008/0194993 A1 | 8/2008 | Mclaren et al. |
| 2008/0208309 A1* | 8/2008 | Saeed ..................... A61F 2/954 623/1.11 |
| 2008/0281398 A1 | 11/2008 | Koss |
| 2008/0306467 A1 | 12/2008 | Reydel |
| 2009/0005679 A1 | 1/2009 | Dala-Krishna |
| 2009/0018526 A1 | 1/2009 | Power et al. |
| 2009/0036780 A1 | 2/2009 | Abraham |
| 2009/0132019 A1 | 5/2009 | Duffy et al. |
| 2009/0171293 A1 | 7/2009 | Yang et al. |
| 2009/0177035 A1 | 7/2009 | Chin |
| 2009/0240253 A1 | 9/2009 | Murray |
| 2009/0254116 A1 | 10/2009 | Rosenschein et al. |
| 2009/0270975 A1 | 10/2009 | Giofford, III et al. |
| 2009/0319017 A1 | 12/2009 | Berez et al. |
| 2010/0016943 A1 | 1/2010 | Chobotov |
| 2010/0024818 A1 | 2/2010 | Stenzler et al. |
| 2010/0030165 A1 | 2/2010 | Takagi et al. |
| 2010/0030256 A1 | 2/2010 | Dubrul et al. |
| 2010/0069852 A1 | 3/2010 | Kelley |
| 2010/0168583 A1 | 7/2010 | Dausch et al. |
| 2010/0185161 A1 | 7/2010 | Pellegrino et al. |
| 2010/0185231 A1 | 7/2010 | Lashinski |
| 2010/0204708 A1 | 8/2010 | Sharma |
| 2010/0211095 A1 | 8/2010 | Carpenter |
| 2010/0268067 A1 | 10/2010 | Razzaque et al. |
| 2010/0272740 A1 | 10/2010 | Vertegel et al. |
| 2010/0298922 A1 | 11/2010 | Thornton et al. |
| 2011/0009943 A1 | 1/2011 | Paul et al. |
| 2011/0034804 A1* | 2/2011 | Hubregtse ......... A61M 25/0082 600/433 |
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0098681 A1 | 4/2011 | Djurivic |
| 2011/0196420 A1 | 8/2011 | Ebner |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0016454 A1* | 1/2012 | Jantzen ................ A61F 2/966 623/1.11 |
| 2012/0020942 A1 | 1/2012 | Hall et al. |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1 | 2/2012 | Whiting et al. |
| 2012/0046690 A1 | 2/2012 | Blom |
| 2012/0169712 A1 | 7/2012 | Hill et al. |
| 2012/0209375 A1 | 8/2012 | Madrid et al. |
| 2012/0221094 A1 | 8/2012 | Cunningham |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0218201 A1 | 8/2013 | Obermiller |
| 2013/0296773 A1 | 11/2013 | Feng et al. |
| 2013/0310823 A1 | 11/2013 | Gelfand et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0114346 A1 | 4/2014 | McCaffrey |
| 2014/0142427 A1 | 5/2014 | Petroff |
| 2014/0214002 A1 | 7/2014 | Lieber et al. |
| 2014/0214048 A1* | 7/2014 | Gulcher ................. A61M 1/74 606/127 |
| 2014/0228808 A1 | 8/2014 | Webster et al. |
| 2014/0276602 A1 | 9/2014 | Bonnette |
| 2014/0358123 A1 | 12/2014 | Kaisha |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0245933 A1 | 9/2015 | Syed |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Van Bladel et al. |
| 2017/0119562 A1* | 5/2017 | Syed ..................... A61F 2/954 |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |
| 2018/0116780 A1 | 5/2018 | Laine |
| 2018/0250147 A1 | 9/2018 | Syed |
| 2019/0091441 A1 | 3/2019 | Syed |
| 2019/0336114 A1 | 11/2019 | Syed |
| 2020/0038210 A1 | 2/2020 | Syed |
| 2021/0196492 A1 | 7/2021 | Bagaoisan |
| 2022/0152347 A1 | 5/2022 | Syed |

FOREIGN PATENT DOCUMENTS

| | | |
|---|---|---|
| CN | 108882975 | 11/2018 |
| CN | 109475722 | 3/2019 |
| CN | 111629696 | 9/2020 |
| EP | 3280355 | 2/2018 |
| EP | 3367969 | 9/2018 |
| EP | 3368123 | 9/2018 |
| EP | 3399944 | 11/2018 |
| EP | 3405261 | 11/2018 |
| EP | 3471815 | 4/2019 |
| EP | 3752104 A1 | 12/2020 |
| IN | 201827018555 | 10/2018 |
| IN | 201827018768 | 10/2018 |
| IN | 201827019509 A | 10/2020 |
| WO | WO 1996/036269 | 11/1996 |
| WO | 1999/40849 A1 | 8/1999 |
| WO | WO 2004/089249 | 10/2004 |
| WO | WO 2010/129193 | 11/2010 |
| WO | WO 2011/011539 | 1/2011 |
| WO | WO 2011/106502 | 9/2011 |
| WO | WO 2011/137336 | 11/2011 |
| WO | WO 2012/030101 | 8/2012 |
| WO | WO 2014/081947 | 5/2014 |
| WO | WO 2014/197839 | 12/2014 |
| WO | WO 2016164215 | 10/2016 |
| WO | WO 2017/074492 | 5/2017 |
| WO | WO 2017/074536 | 5/2017 |
| WO | WO 2017/127127 | 7/2017 |
| WO | WO 2017/222571 | 12/2017 |
| WO | WO 2017/222612 | 12/2017 |
| WO | WO 2018/164766 | 9/2018 |
| WO | WO 2019/070349 | 4/2019 |

OTHER PUBLICATIONS

International Search Report and Written Opinion for PCT/US2016/024794 dated Jul. 1, 2016, 10 pages.
International Search Report and Written Opinion for PCT/US2016/024795 dated Aug. 30, 2016, 14 pages.
International Search Report and Written Opinion for PCT/US2016/047163 dated Oct. 28, 2016, 9 pages.
International Search Report and Written Opinion for PCT/US2016/047165 dated Jan. 5, 2017, 13 pages.
International Search Report and Written Opinion for PCT/US2017/021188 dated May 10, 2017, 11 pages.

(56) References Cited

OTHER PUBLICATIONS

International Search Report and Written Opinion for PCT/US2018/012834 dated Mar. 15, 2018, 13 pages.
International Search Report and Written Opinion for PCT/US2018/047372 dated Jan. 2, 2019, 8 pages.
International Search Report and Written Opinion for PCT/US2019/012727 dated Mar. 21, 2019, 12 pages.
International Search Report and Written Opinion for PCT/US2019/12745 dated Apr. 1, 2019, 10 pages.
International Preliminary Report on Patentability for PCT/US2013/071271 dated May 26, 2015, 6 pages.
International Preliminary Report on Patentability for PCT/US2016/024795 dated May 1, 2018, 10 pages.
International Preliminary Report on Patentability for PCT/US2016/047165 dated May 1, 2018, 5 pages.
International Preliminary Report on Patentability for PCT/US2017/021188 dated Dec. 25, 2018, 9 pages.
International Preliminary Report on Patentability for PCT/US2016/047163 dated Dec. 25, 2018, 7 pages.
EP 16777055.1 Extended Search Report dated Feb. 12, 2019, 7 pages.
EP 18725097.2 Extended Search Report dated Apr. 24, 2019, 9 pages.
EP 16860437.9 Extended Search Report dated May 17, 2019.
EP 16906475.5 Extended Search Report dated Jan. 24, 2020.
EP 17815838.2 Extended Search Report dated Jan. 20, 2020.
Beckman et al., Venous Thromboembolism: A Public Health Concern, Am J Prev Med., 2010, vol. 38(4), pp. S495-501.
Blaney et al., Alteplase for the Treatment of Central Venous Catheter Occlusion in Children: Results of a Prospective, Open-Label, Single-Arm Study (The Cathflo Activase Pediatric Study), J Vasc Interv Radiol, 2006, vol. 17(11), pp. 1745-1751.
Godwin, J., The Circulatory and Respiratory Systems, Z0250 Lab III, 2002, retrieved from: https://projects.ncsu.edu/cals/course/zo250/lab-3.html.
Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.
Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.
Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.
Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
Stroke Treatments, American Heart Association, Retrieved from: http://www.strokeassociation.org/STROKEORG/AboutStroke/Treatment/Stroke-Treatments_UCM_310892_Article.jsp#V9Hrg2WfV_1 on Sep. 8, 2016.

* cited by examiner

| Insert a snare wire with a 20-30 mm snare at its distal end through a small 4Fr stabilization sheath inserted through a snare access sheath providing an ipsilateral retrograde access into the femoral artery and direct it to the aortic bifurcation.   S901 |
|---|

↓

| Using a main access sheath of 7Fr. Lumen to establish a contralateral retrograde access and advance a large sheath catheter, typically Fr. 7, up the femoral artery and guide it to the aortic bifurcation, using radiographic imaging.   S902 |
|---|

↓

| Insert through the main sheath catheter, the modified bifurcated catheter (M-Y Sheath) having a fixed flat wire with a stabilization wire extension to the flat wire emerging through a side exit hole 2-4cm prior to the distal end of the bifurcated catheter, the stabilization wire having a length of 6 to 13 cm.   S903 |
|---|

↓

| The stabilization wire extension of the fixed flat wire is captured by the snare at the aortic bifurcation.   S904 |
|---|

↓

| Optionally: Advance a reverse curve catheter through the lumen of the bifurcated catheter (M-Y sheath) to assist in accessing the ipsilateral illiac artery over the aortic bifurcation.   S905 |
|---|

↓

| The snare wire with the fixed wire attached is pulled back with the small stabilization sheath, pulling the bifurcated catheter behind it over the reverse curve catheter into the contralateral common illiac artery over the aortic bifurcation.   S906 |
|---|

↓

| A push on the bifurcated catheter from its proximal end is used to reduce any tension on the catheter as it is pulled by the stabilization wire extension and increase ease of access.   S907 |
|---|

↓

| M-Y sheath is pulled down using the snare wire, till the exit hole of the stabilization wire is at the contralateral access and the stabilization wire is externalized through the contralateral access.   S908 |
|---|

↓

| A tension is applied to the fixed Flat wire at the proximal end of the bifurcated catheter at the contralateral access with the stabilization wire locked in place providing end to end stability and tension to the bifurcated catheter.   S910 |
|---|

↓

| The optional reverse curve catheter if used and any dialator used are removed from the bifurcated catheter.   S911 |
|---|

↓

| The bifurcated catheter is ready for accepting procedural catheters and instruments for procedure with stabilization and tension provided by the locked stabilization wire and the fixed flat wire at the proximal end of the bifurcated catheter.   S912 |
|---|

Figure 9

MODIFIED FIXED FLAT WIRE BIFURCATED CATHETER AND ITS APPLICATION IN LOWER EXTREMITY INTERVENTIONS

CROSS REFERENCE TO RELATED APPLICATIONS

This application is a continuation of U.S. patent application Ser. No. 16/183,066, entitled "A MODIFIED FIXED FLAT WIRE BIFURCATED CATHETER AND ITS APPLICATION IN LOWER EXTREMITY INTERVENTIONS," and filed on Nov. 7, 2018, which claims priority under 35 U.S.C. § 119 to U.S. Provisional Application No. 62/631,904, entitled "MODIFIED FIXED FLAT WIRE BIFURCATED CATHETER AND ITS APPLICATION IN AORTO BIFEMORAL BYPASS," and filed on Feb. 18, 2018, the contents of each of which are hereby incorporated by reference in their entirety.

TECHNICAL FIELD

The present disclosure relates to improved methods and apparatuses for traversing a tortuous vasculature. Specifically, the present disclosure relates to providing support to procedural catheters during lower extremity intervention procedures to traverse the procedural site through the tortuous access vessels.

BACKGROUND

Technology associated with interventional procedures is ever developing, particularly in the areas of stenting and balloon angioplasty of Interventional procedures are typically challenging, as accessing various regions of the artery can be dependent on the anatomical disposition of the access location. Specifically, accessing regions of a tortuous peripheral arteries and performing interventional procedures in a hostile anatomy can be very difficult. Furthermore, the subsequent removal of blockages and placement of a stent delivery system into aorto femoral arteries becomes more difficult, or in some instances impossible. The interventional procedure may also be difficult for the popliteal and tibial arteries. The stenting procedure is meant to re-establish a more normalized blood flow through these tortuous arteries by opening up regions constricted by plaque or embolic deposits, which inhibit blood flow.

Although the stent delivery systems are designed to accommodate very acute bends, they are reliant upon guide catheters, guide wires and/or embolic protection devices during deployment. When long delivery systems in tortuous arteries the pushability of catheters and guide wires become critical. As a result, the rigid or stiff catheters and guide wires are needed to manipulate the tortuous entry. With these type of rigid devices, injuries to the tortuous arteries and access vessels often occur during the insertion, manipulation and stabilization of the stent delivery mechanism. Injuries to the tortuous arteries and access vessels often occur during removal of the guide wires, secondary equipment and wires as well. Specifically, the injuries can be caused by puncturing or cutting into the arterial walls resulting in dissections and trauma to the vessels involved. These traumas can be dangerous to the patient as they can ultimately affect blood flow by leakage at the dissections. In some instances, the traumas can create accumulation of thrombus, which is an organization of white blood cells. Dissections and the accumulation of thrombus can require additional procedures to repair and heal the damaged artery walls.

In view of the foregoing, there exists a need to provide a simplified procedure that reduces the injuries caused to the arterial walls during lower extremity interventions. Furthermore, there exists a need to for a usable sheath and catheter stabilization system than enable the use of softer catheters and less stiff guide wires for the treatment of lower extremities.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings.

FIG. 9 illustrates a process for providing stability, tension and pushability of the bifurcated catheter, in accordance with an embodiment of the disclosure.

DETAILED DESCRIPTION OF ILLUSTRATED EMBODIMENTS

The present invention is described with reference to the attached figures, where like reference numerals are used throughout the figures to designate similar or equivalent elements. The figures are not drawn to scale, and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present disclosure.

The present disclosure provides a system and method for providing access to tortuous arteries to perform lower extremity interventions. The present disclosure is directed towards employing a flat fixed wire bifurcated catheter. The flat fixed wire bifurcated catheter includes a flat wire fixed along the length of the bifurcated catheter from its proximal end to the bifurcation. The flat wire can emerge from a side hole at the bifurcation end of the bifurcated catheter to extend for an additional length beyond the bifurcation. The distal end of the bifurcated catheter can be configured to have a dual lumen (e.g., a large procedural lumen and a small stabilization lumen) from which the flat wire emerges. Alternatively, the distal end of the bifurcated catheter can be configured to have a procedural lumen and a side hole for the stabilization wire.

A small sheath can be provided to enable percutaneous access for the distal end of the support wire. A push and pull force can be applied to the bifurcated catheter to enable the bifurcated catheter to traverse the tortuous vessels to the site of the bifemoral bypass location. This process allows the bifurcated catheter to be positioned in either the common femoral artery or the proximal superficial femoral artery. Furthermore, the stabilization wire can be locked at the accesses to apply tension and stabilization to the procedural lumen.

It should be understood by one of ordinary skill in the art, that the disclosed apparatus can be implemented in any type of lower extremity peripheral arterial intervention. In addition, the disclosed apparatus can be implemented within the internal iliac artery vascular distribution (e.g., uterine artery embolization, prostate artery embolization, proximal internal iliac artery embolization prior to endovascular common iliac artery aneurysm repair, etc.). The disclosed system and method can reduce injury to the vessels within the arteries, reduce trauma caused during the intervention procedure, and improve the procedural success rate. The disclosed system and method can also improve navigation speed through difficult anatomy and enhance stability.

Figure 1:
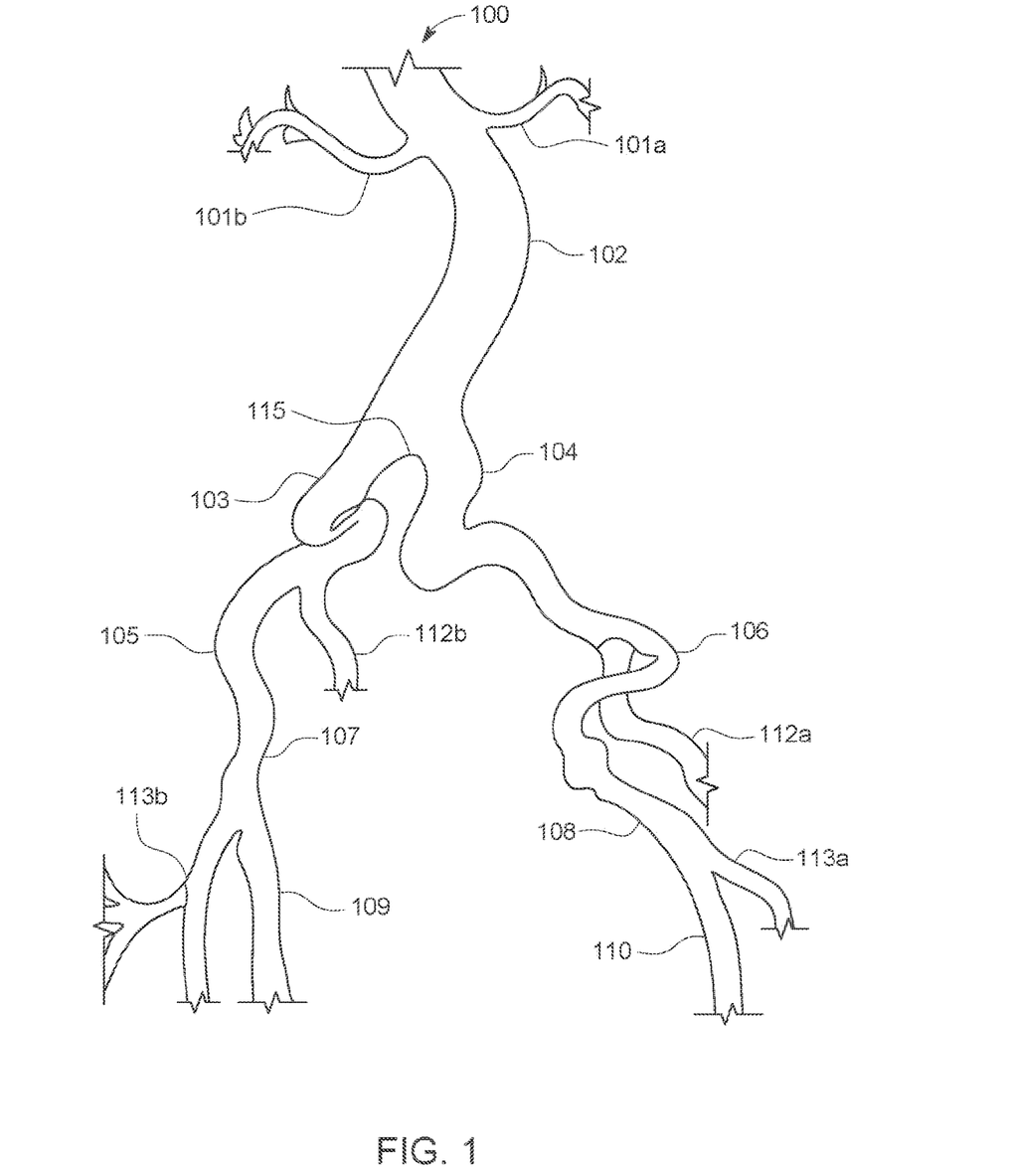
FIG. 1 illustrates tortuous arteries of the lower extremities, in accordance with an embodiment of the disclosure.

FIG. 1 illustrates an exemplary tortuous vessel artery 100, in accordance with an embodiment of the disclosure. The tortuous vessel artery 100 can include an abdominal aortic bifurcation with tortuous branch arteries. The tortuous branch arteries can include a right renal artery 101b and a left renal artery 101a extending from an abdominal aorta 102. The abdominal aorta 102 can be parted at an aortic bifurcation 115, and connected to arteries of the lower limbs. The arteries of the lower limbs can include a right common iliac 103 and a left common iliac 104. The left common iliac 104 can be split into a left external iliac 106 and a left internal iliac 112a. The left external iliac 106 can be connected to a left common femoral 108, and further split into a left deep femoral 113a, and a left superficial femoral 110. The The right common iliac 103 can be split into a right external iliac 105 and a right internal iliac 112b. The right external iliac 105 can be connected to a right common femoral 107, which splits into a right deep femoral 113b and a right superficial femoral 109. FIG. 1 illustrates the tortuous nature of the peripheral arteries.

When performing interventions within the tortuous vessel artery 100, it is common to encounter difficulties associated with pushability and torque. As the catheters and wires are guided over a highly angulated aortic bifurcation 115 or through the extremely tortuous common iliac arteries 103 and 104, it can be extremely difficult to apply torque. Furthermore, these arteries can contain calcific plaques or other obstructions which can add anatomic and technical challenges with traversing the tortuous vessel artery 100.

Figure 2:
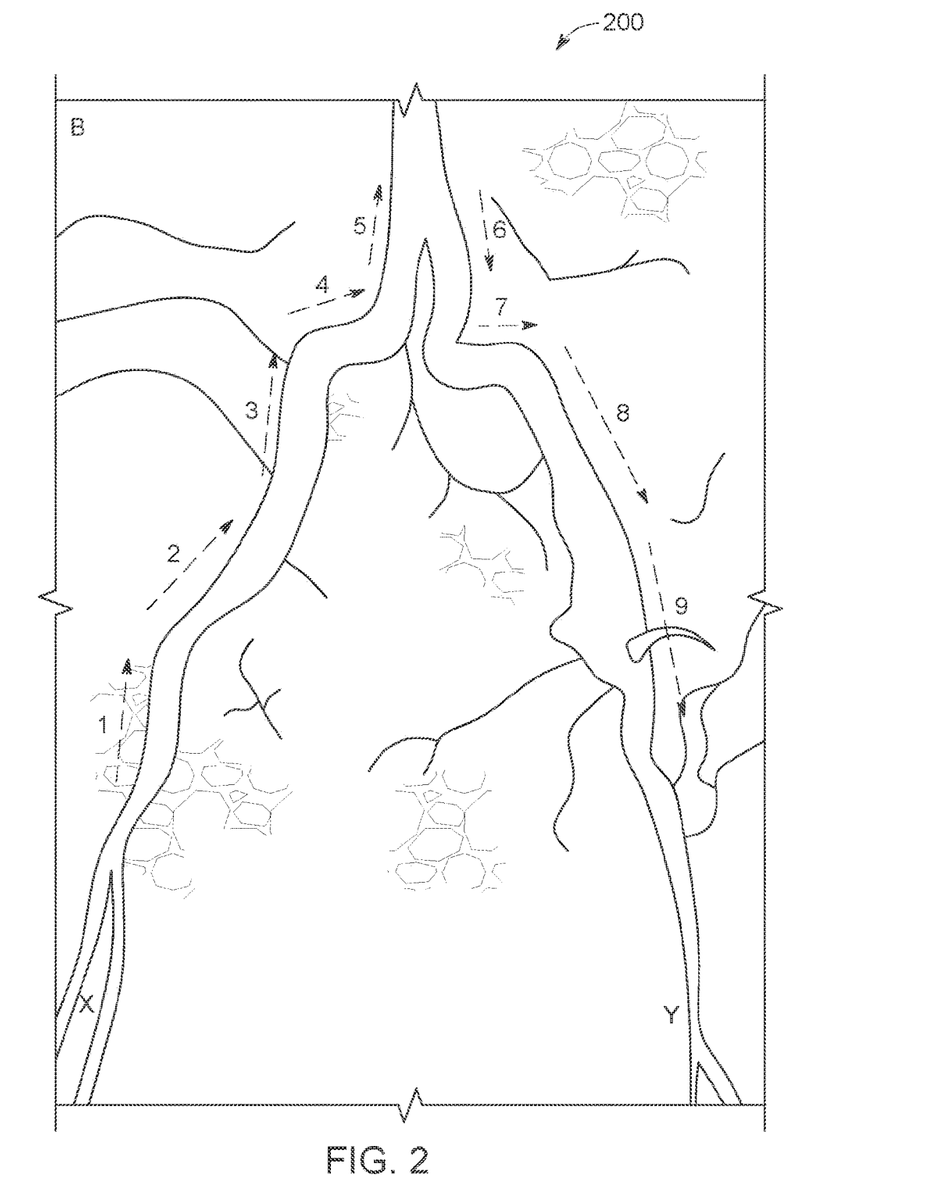
FIG. 2 illustrates a tortuous anatomical pathway from the percutaneous access within the common femoral artery to a potential procedure location on the ipsilateral side, in accordance with an embodiment of the disclosure.

FIG. 2 illustrates a tortuous anatomical pathway 200 from the percutaneous access within the common femoral artery to a potential procedure location on the ipsilateral side, in accordance with an embodiment of the disclosure. In some embodiments, interventional devices such as wires and catheters are pushed from the contralateral access at point 'X' to the treatment site 'Y'. The devices would need to travel through the general pathways 1 through 9. Due to the multi directional twists and turns along the pathways 1 through 9, the devices can suffer from a significant loss of performance such as torque and pushability. While FIG. 2 illustrates the tortuous anatomical pathway 200 in a two-dimensional format, the tortuosity of the anatomical pathway 200 is often significantly more severe, as illustrated in FIG. 1.

Figure 3:
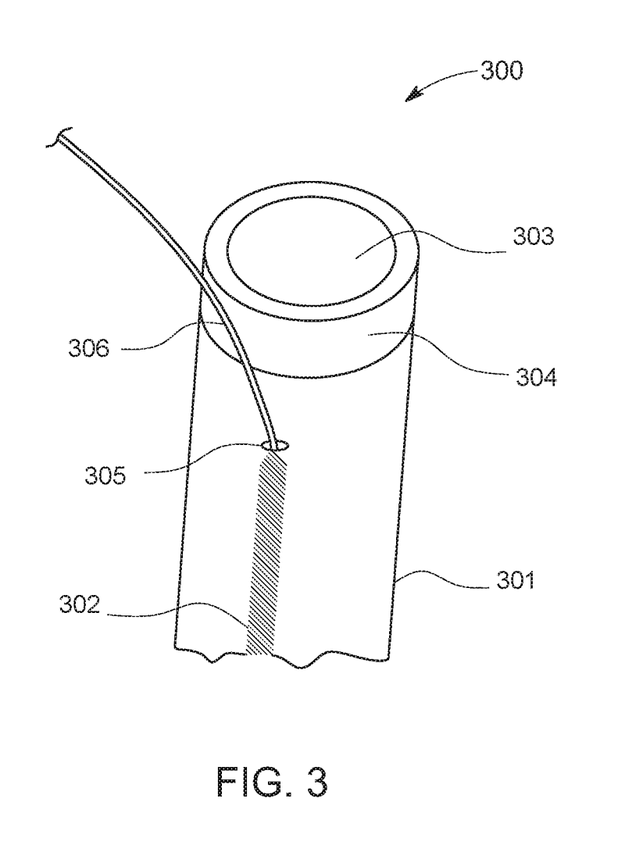
FIG. 3 illustrates a fixed flat-wire bifurcated catheter, in accordance with an embodiment of the disclosure.

FIG. 3 illustrates a bifurcated catheter 300, in accordance with an embodiment of the disclosure. The bifurcated catheter 300 can include a bifurcated sheath 301 and a fixed flat-wire 302. The fixed flat wire 302 can be integrated within the bifurcated catheter 300. This is discussed in greater detail below.

The bifurcated catheter can have a proximal end (not shown) and a distal end. The distal end can include a side hole 305 for a stabilization wire. The fixed flat wire 302 can be extended from the proximal end (not shown) of the bifurcated catheter 300 to the side hole 305. The bifurcated catheter 300 can also include a bifurcated sheath 301 that spans almost the entire length of the bifurcated catheter 300. In some embodiments, the bifurcation sheath 301 is approximately 2 centimeters from the distal end of the bifurcated catheter 300. For example, in some embodiments the bifurcated catheter 300 can include a radio opaque band 304 at its distal end that limits the length of the bifurcated sheath 301.

The radio opaque band 304 can be implemented to track the distal end of the bifurcated catheter 300 as it is advanced through the arteries of FIG. 1. The bifurcated catheter 300 can also have a procedural lumen 303. In some embodiments, the procedural lumen 303 can extend from its proximal end to its distal end. The bifurcated catheter 300 can also have a stabilization wire 306. The stabilization wire 306 can be configured to protrude from the bifurcated catheter 300 at the side hole 305. In some embodiments, the stabilization wire 306 can extend up to 10 cm beyond the end of the bifurcated catheter 300.

Furthermore, the stabilization wire 306 can be a flat wire or a round wire. For example, the stabilization wire 306 can be made up of a solid or hollow member with a cross-section that is round, flat, rectangular, or a combination thereof. The stabilization wire 306 can be fabricated using commonly known materials in the art including, for example, stainless steel, nickel titanium, composites, metal reinforced polymer, polymer, a combination thereof, or the like.

FIGS. 4 to 8 illustrate an exemplary process for lower extremity intervention implementing the bifurcated catheter 300 of FIG. 3. The lower extremity intervention can include, for example, an Aorto Bifemoral Bypass or a tortuous aortoiliac artery treatment. Furthermore, FIGS. 4 to 8 illustrate the process of providing end-to-end stability to any additional procedural catheter and instruments introduced through the procedural lumen 303 of the bifurcated catheter 300.

Figure 4:
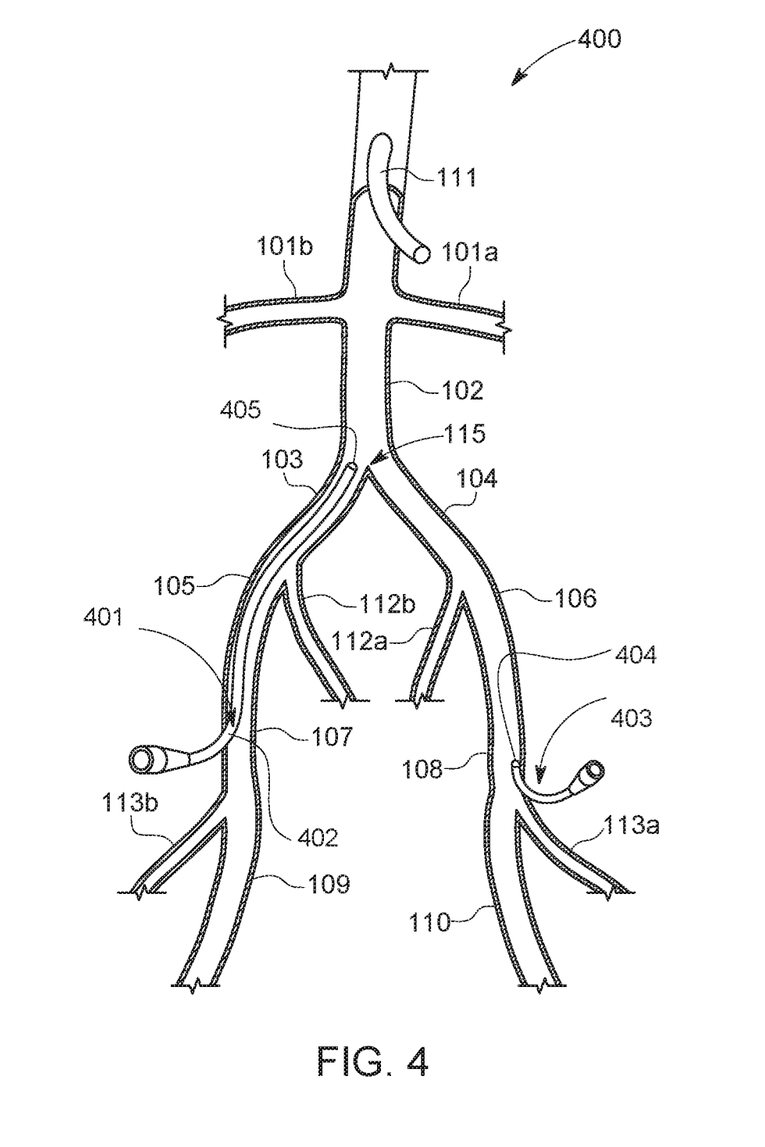
FIG. 4 illustrates the fixed flat-wire catheter in the commission of an interventional process, in accordance with one embodiment of the disclosure.

FIG. 4 illustrates a diagram 400 where a percutaneous contralateral femoral access 402 is introduced into the right common femoral artery 107. The percutaneous contralateral femoral access 402 can be implemented to introduce a main access sheath 401 into the right common femoral artery 107. The main access sheath 401 can be configured as a 7 Fr. vascular sheath. The main access sheath 401 can be advanced through the right external 105 and right common iliac 103 to the aortic bifurcation 115. The main access sheath 401 can be tracked using the radio opaque band 304 as the main access sheath 401 is advanced to the aortic bifurcation 115. FIG. 4 also illustrates the introduction of a percutaneous ipsilateral femoral access 404 into the left common femoral artery 108. The percutaneous ipsilateral femoral access 404 can be introduced for a snare access sheath 403 of a 4 Fr. internal lumen.

Figure 5:
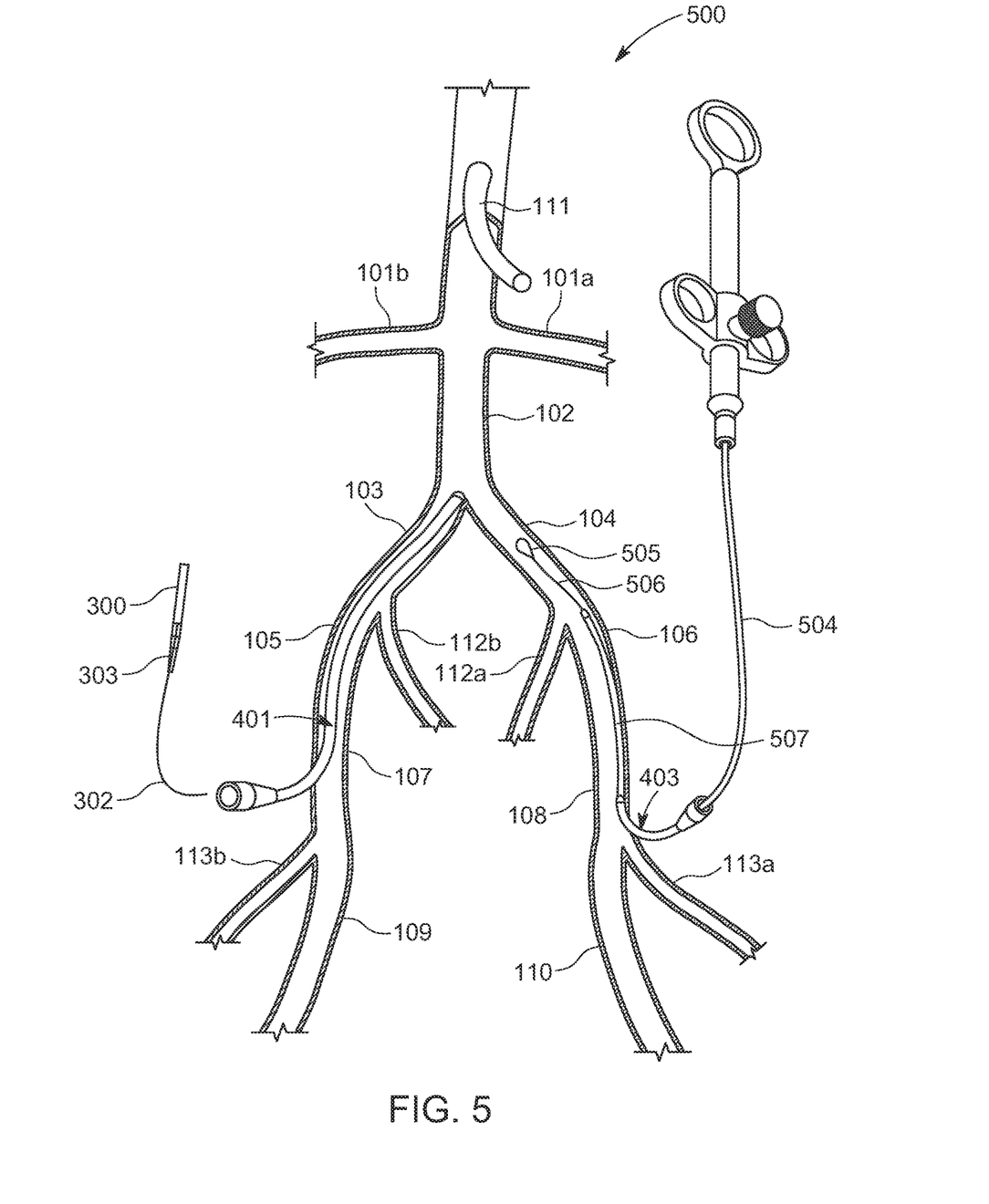
FIG. 5 illustrates a process for introducing a snare catheter and extending a snare wire to an aortic bifurcation, in accordance with an embodiment of the disclosure.

FIG. 5 illustrates a process for introducing a snare catheter and extending a snare wire to an aortic bifurcation, in accordance with an embodiment of the disclosure. Once the access sheaths 401 and 403 are in place, a 4 Fr snare sheath 504 and snare wire 506 can be introduced through the retrograde snare access sheath 403. In some embodiments, the snare wire 506 can include a snare 505 at its distal end extending to the aortic bifurcation 115. The snare 505 can be 20 to 30 mm (or smaller) in length. In some embodiments, the fixed flat wire bifurcated catheter 300 can include a dialator 503 in the main sheath. The fixed flat wire bifurcated catheter 300 and the stabilization wire 306 can be introduced through the main access sheath 401. The main access sheath 401 can include a distal end, labeled as the tip of the sheath aligned to the aortic bifurcation. FIG. 5 further illustrates the fixed flat wire bifurcated catheter 300 and the stabilization wire 306 being pushed through the distal end of the main sheath 401. The stabilization wire 306 can be extended out of the distal end of the main sheath 401 to be captured at the distal end of the snare 505.

Figure 6:
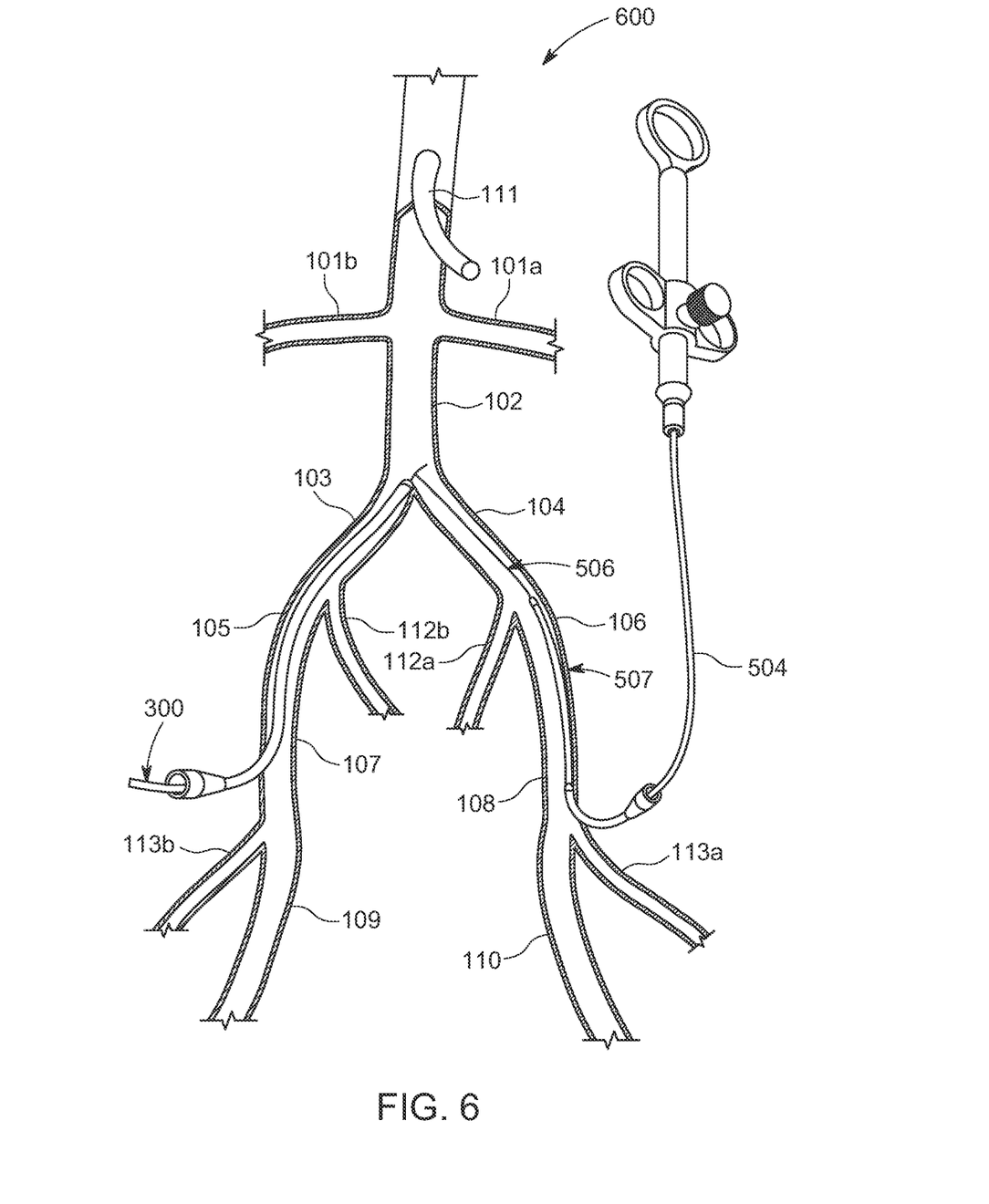
FIG. 6 illustrates a process for inserting a fixed stabilization wire into a main sheath and capturing a stabilization wire extension, in accordance with an embodiment of the disclosure.

FIG. 6 illustrates a process for inserting a fixed stabilization wire into a main sheath and capturing a stabilization wire extension, in accordance with an embodiment of the disclosure. The stabilization wire 306 can be tightened to a snare knot 601. A pull force 703 can be applied to the distal end of the bifurcated catheter 300. The pull force 703 can be derived from the snare catheter 504 and the snare wire 506, which has snared the stabilization wire 306. A push force 701 can be applied on the proximal end of the bifurcated catheter 300. The push force 701 and the pull force 703 can be applied simultaneously. The push force 701 and the pull force 703 guides the distal end of the bifurcated catheter 300 with the dilator tip 503 over the aortic bifurcation and down the ipsilateral left iliac arteries 104 and 105.

Figure 7:
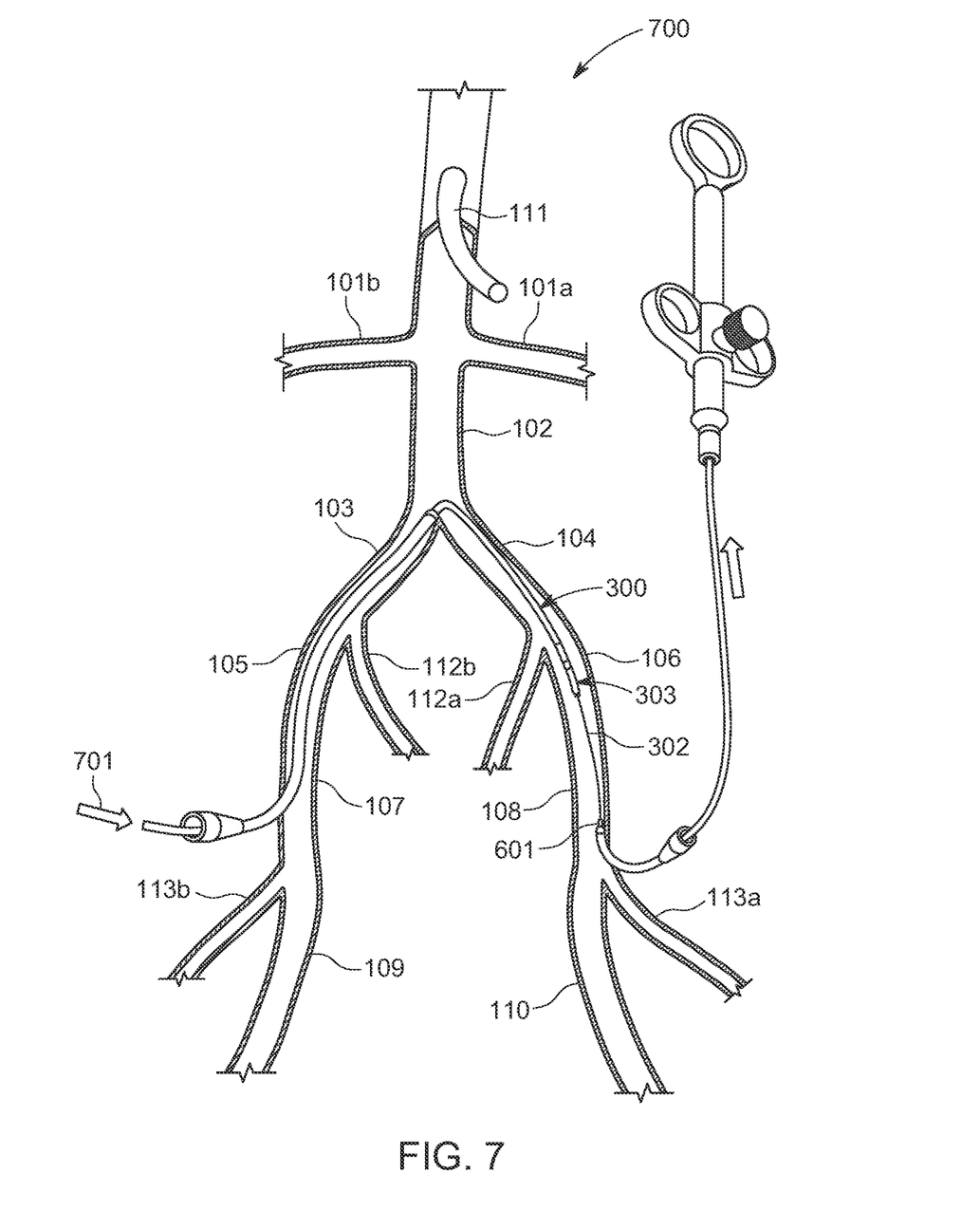
FIG. 7 illustrates a process for advancing the bifurcated catheter into the ipsilateral iliac artery, in accordance with one embodiment of the disclosure.

FIG. 7 illustrates a process for advancing the bifurcated catheter into the ipsilateral iliac artery, in accordance with one embodiment of the disclosure. Once guided over the aortic bifurcation and down the ipsilateral left iliac arteries 104 and 105, the bifurcated catheter 300 can be guided to the left common femoral artery 108. The snare wire 506, encompassing the snared stabilization wire 306, can be pulled out of the ipsilateral snare access sheath 403 and anchored.

Figure 8:
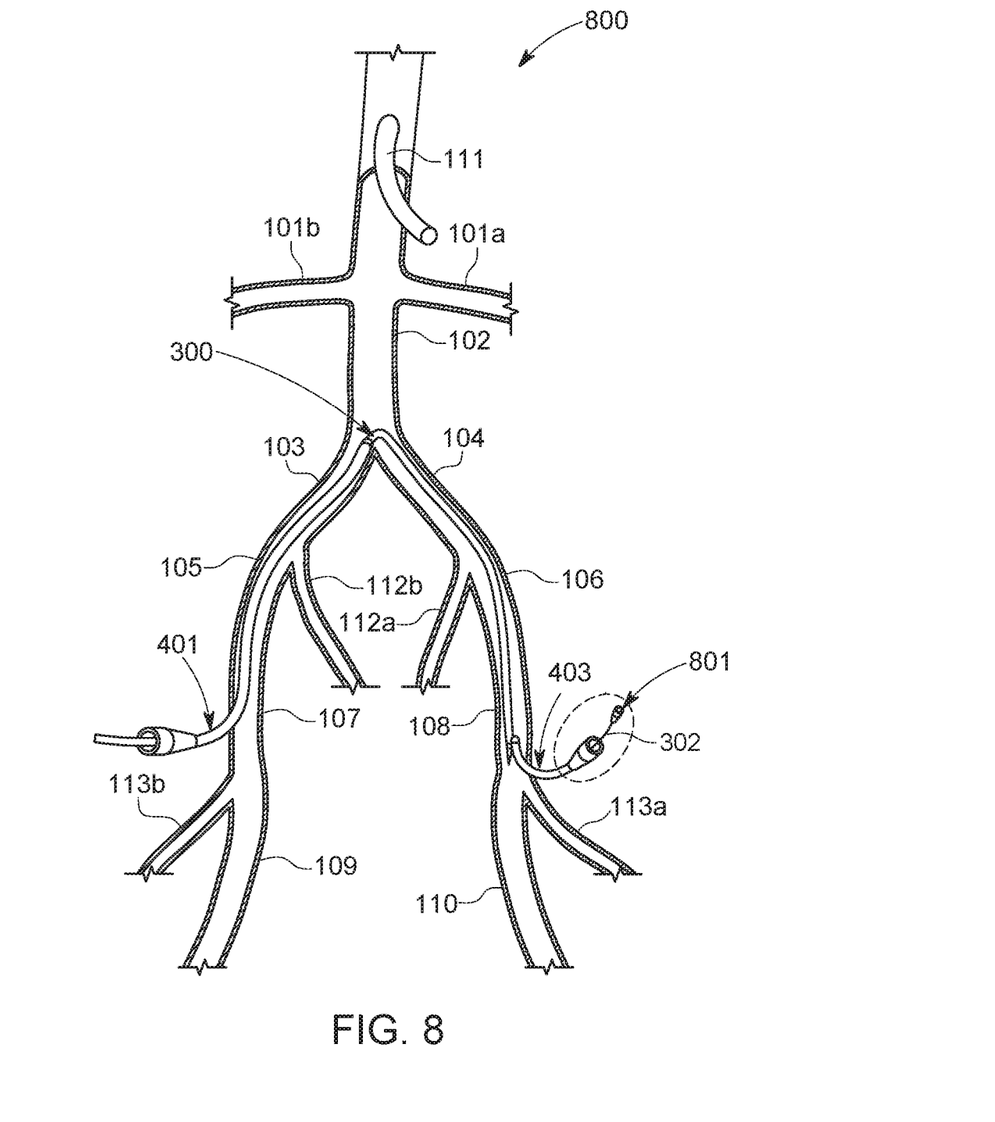
FIG. 8 illustrates a process for advancing the bifurcated catheter into the ipsilateral femoral artery with the stabilization wire externalized and anchored, in accordance with one embodiment of the disclosure.

FIG. 8 illustrates a process for advancing the bifurcated catheter into the ipsilateral femoral artery with the stabilization wire externalized and anchored, in accordance with one embodiment of the disclosure. The snare wire 506 can be anchored with the snared stabilization wire 306 locking the snare wire external to the snare access sheath. The snare wire can be locked to the snare access sheath using a wire lock 801. By locking the stabilization wire 306 outside the snare access 403 and providing a pull force on the distal end of the bifurcated catheter, a tension can be applied to the main procedural lumen 303. This tension can provide stabilization to the main procedural lumen 303. Any procedural catheters and instruments within the main procedural lumen 303 can also be stabilized. Anchoring and locking the stabilization wire can cause bifurcation of the bifurcated catheter at the snare access sheath. This bifurcation can provide an anchor point for improved pushability to the procedural catheters.

FIG. 9 illustrates a process 900 for providing stability, tension and pushability of the bifurcated catheter of FIG. 3, in accordance with an embodiment of the disclosure.

At step 901, a small 4 Fr lumen snare access sheath is inserted into the left common femoral artery to provide an ipsilateral retrograde access. A snare catheter is inserted through the snare access sheath with a snare wire. The snare catheter can be 4 Fr or smaller. The snare wire can have a 20-30 mm snare at its distal end. In some embodiments, the snare wire can have a snare less than 20 mm at its distal end. The snare wire can be guided to the aortic bifurcation.

At step 902, a main access sheath can be used to establish a contralateral retrograde access at the right common femoral artery location. The main access sheath can be a 7 Fr. Lumen. A large sheath catheter can be advanced up the right femoral artery and the iliac arteries towards the aortic bifurcation. The large sheath catheter can be guided using radiographic imaging. The large sheath catheter can be Fr.7.

At step 903, a modified bifurcated catheter can be inserted into the main sheath and guided to the aortic bifurcation. The modified bifurcated catheter can have a fixed flat wire secured to the bifurcated catheter, from its proximal end to the bifurcation. An extension of the flat wire can emerge through a side exit hole at the bifurcation. The extension can be the stabilization wire. The side exit hole at the bifurcation can be between 2-4 cm prior to the distal end of the bifurcated catheter. In some embodiments, the stabilization wire can have a length of 6 to 13 cm beyond the side exit hole. In alternative embodiments, the stabilization wire can be extended beyond 13 cm from the side exit hole.

At step 904 the stabilization wire, extending from the side exit hole, can be captured by the snare of the snare wire. The snare wire can capture the stabilization wire at the aortic bifurcation. The snare can be tightened to secure the stabilization wire and apply a pull pressure on it.

At step 905 a reverse curve catheter can be inserted through the main lumen of the bifurcated catheter to access the left common iliac artery. The reverse curve catheter can assist in transitioning the bifurcated catheter from the contralateral right common iliac artery to the ipsilateral left common iliac artery over the aortic bifurcation.

At step 906, an external pull force can be applied on the snare wire with the stabilization wire snared. The pull force can be accomplished by implementing a small stabilization sheath. By pulling the small stabilization sheet, the attached fixed flat wire and the main lumen are also pulled over the reverse curve catheter into the contralateral common left iliac artery.

At step 907 a push force is applied on the bifurcated catheter at its proximal end to assist advance the bifurcated catheter past sharp corners and reduce tension on the catheter as it is pulled by the stabilization wire. The combination of the push and pull force enable the bifurcated catheter to easily overcome obstructions as it traverses tortuous curves of the vessels. The combination of push and pull forces also help to reduce the tension on the bifurcated catheter and increase access while reducing the trauma to the vessels.

At step 908 the bifurcated sheath is simultaneously pulled and pushed down the ipsilateral left side vasculature, until the side exit hole of the stabilization wire is at the ipsilateral snare access sheath location. The stabilization wire is externalized by pulling the snare wire out of the access sheath through the ipsilateral access.

At step 909 the externalized stabilization wire is anchored by locking it in place at the ipsilateral access by a wire lock. The modified bifurcated catheter is anchored at the distal end of the bifurcation.

At step 910, a tension is applied to the fixed Flat wire at the proximal end of the bifurcated catheter. The tension is applied at the contralateral access with the stabilization wire. The stabilization wire can be locked in place at the distal end. An end-to-end application of tension can be applied to provide stability to the bifurcated catheter. This stability increases pushability of any procedural catheters within its main procedural lumen.

At step 911 any optional reverse curve catheter can be used. Furthermore, any dialator used to reduce trauma to vessels can be removed from the bifurcated catheter.

At step 912 the bifurcated catheter is configured to accept the procedural catheters and instruments for procedure, through its main lumen. Stabilization and tension can be provided by the locked stabilization wire at the distal end of the bifurcation and the fixed flat wire. The bifurcated catheter is configured for interventional procedures (stents, atherectomy, etc.) within the left peripheral vasculature. The process 900 is terminated after step 912.

The examples provided herein are directed towards specific examples. One of ordinary skill in the art would understand the provided examples are not intended to be exhaustive. There exists other exemplary access and stabilization of a procedural catheter or sheath. As is well understood, the preferred method will vary based on the location of the procedure and the physical condition of the patient.

As is well understood by those familiar with the art, the invention may be embodied in other specific forms without departing from the spirit or essential characteristics thereof. Likewise, the naming and division of the members, features, attributes, and other aspects are not mandatory or significant, and the mechanisms that implement the invention or its features may have different structural construct, names, and divisions. Accordingly, the disclosure of the invention is intended to be illustrative, but not limiting, of the scope of the invention.

The embodiments disclosed herein can be implemented as hardware, firmware, software, or any combination thereof. Moreover, the software is preferably implemented as an application program tangibly embodied on a program storage unit or computer readable medium. The application program may be uploaded to, and executed by, a machine comprising any suitable architecture.

The invention claimed is:

1. A system comprising:
   a bifurcated catheter comprising a proximal end, a distal end and a bifurcation between the proximal end and the distal end, the bifurcated catheter further comprising a side hole near the distal end of the bifurcated catheter;
   a stabilization wire attached to a wall of the bifurcated catheter,
   a snare access sheath; and
   a snare catheter configured to be inserted through the snare access sheath, the snare catheter comprising a snare wire,
   wherein the snare wire is configured to snare a distal end of the stabilization wire,
   wherein the stabilization wire is configured to emerge and extend from the side hole and wherein the stabilization wire is configured to be pulled to guide and stabilize the bifurcated catheter, and
   wherein the snare wire is configured to be externalized to lock the distal end of the stabilization wire at a first location and wherein the bifurcated catheter is configured to be locked at a second location to apply tension to the bifurcated catheter.

2. The system of claim 1, wherein the bifurcation is 2 cm from the distal end of the bifurcated catheter.

3. The system of claim 1, wherein the stabilization wire is configured to extend at least 10 cm beyond the bifurcation.

4. The system of claim 1, wherein the bifurcated catheter further comprises a procedural lumen and a stabilization lumen.

5. The system of claim 4, wherein the stabilization wire is configured to emerge from the stabilization lumen at the side hole.

6. The system of claim 4, wherein the procedural lumen is larger than the stabilization lumen.

7. The system of claim 1, wherein the bifurcated catheter is configured for arterial access via a percutaneous contralateral arterial access.

8. The system of claim 1, wherein the bifurcated catheter comprises a procedural lumen, and wherein the stabilization wire is configured to emerge from the procedural lumen at the side hole.

9. The system of claim 1, further comprising a sheath configured to provide percutaneous ipsilateral access for a distal end of the stabilization wire.

10. The system of claim 1, wherein the bifurcated catheter is configured to receive a pull force and a push force to advance the bifurcated catheter through tortuous vessels to a site of a lower extremity intervention procedure.

11. The system of claim 1, wherein the stabilization wire is configured to apply tension and stabilization to the procedural lumen for access to a procedural location.

12. The system of claim 1, wherein the stabilization wire comprises a fixed wire portion attached to the bifurcated catheter and wherein the portion of the stabilization wire that emerges from the side hole comprises a stabilization wire extension.

13. The system of claim 1, wherein the bifurcated catheter comprises a radio opaque band.

14. The system of claim 1, wherein the proximal end of the stabilization wire is affixed to the bifurcated catheter at the second location and wherein the distal end of the stabilization wire extends from the side hole beyond the distal end of the bifurcated catheter.

15. The system of claim 14, wherein a combination of push and pull forces are configured to be applied to the bifurcated catheter by the stabilization wire.

16. The system of claim 1, wherein the snare wire is configured to snares the distal end of the stabilization wire using a snare knot.

17. A system comprising:
   a bifurcated catheter comprising a proximal end, a distal end and a bifurcation between the proximal end and the distal end, the bifurcated catheter further comprising a procedural lumen; and a stabilization wire attached to a wall of the procedural lumen, a snare access sheath; and a snare catheter configured to be inserted through the snare access sheath, the snare catheter comprising a snare wire, wherein the snare wire is configured to snare a distal end of the stabilization wire, wherein the stabilization wire extends within the procedural lumen from the proximal end to the distal end of the bifurcated catheter and further extends beyond the distal end of the bifurcated catheter, and wherein the snare wire is configured to be externalized to lock the distal end of the stabilization wire at a first location and wherein the bifurcated catheter is configured to be locked at a second location to apply tension to the bifurcated catheter.

18. The system of claim 17, wherein a proximal end of the stabilization wire is affixed to the bifurcated catheter at the second location and wherein the distal end of the stabilization wire extends from a side hole beyond the distal end of the bifurcated catheter.

19. The system of claim 18, wherein a combination of push and pull forces are configured to be applied to the bifurcated catheter by the stabilization wire.

20. The system of claim 17, wherein the snare wire is configured to snare the distal end of the stabilization wire using a snare knot.

* * * * *